United States Patent [19]  [11]  4,339,421
Schultess et al.  [45]  Jul. 13, 1982

[54] SYNTHETIC MAGNESIUM ALUMINOSILICATE, PROCESS FOR THE MANUFACTURE THEREOF, AND PHARMACEUTICAL COMPOSITIONS CONTAINING SAME

[75] Inventors: Adrian Schultess; Jean-Claude Farine, both of Suisse, Switzerland

[73] Assignee: Laboratoires OM Societe Anonyme, Meyrin, Switzerland

[21] Appl. No.: 69,542

[22] Filed: Aug. 24, 1979

[30] Foreign Application Priority Data

Sep. 7, 1978 [CH] Switzerland ............... 9384/78
Jun. 22, 1979 [CH] Switzerland ............... 5890/79

[51] Int. Cl.³ .................... A61K 33/06; A61K 33/12; C01B 33/28
[52] U.S. Cl. .................... 423/330; 424/154; 424/155; 423/118; 423/329
[58] Field of Search .............. 424/155, 327, 154; 423/118, 328, 330

[56] References Cited

U.S. PATENT DOCUMENTS

| | | | |
|---|---|---|---|
| 2,384,563 | 9/1945 | Roseman et al. | 424/155 |
| 2,970,889 | 2/1961 | Ishino et al. | 424/155 |
| 2,990,247 | 6/1961 | Conard et al. | 424/155 |
| 3,032,394 | 5/1962 | Ishino et al. | 424/155 |
| 3,636,200 | 1/1972 | Zentner | 424/155 |
| 3,767,794 | 10/1973 | McVean et al. | 424/155 |
| 4,108,984 | 8/1978 | Sato | 424/155 |

FOREIGN PATENT DOCUMENTS

| | | | |
|---|---|---|---|
| 1667490 | 7/1971 | Fed. Rep. of Germany | 424/155 |
| 53CAM | 6/1964 | France | 424/155 |
| 59294 | 2/1970 | Poland | 424/155 |
| 925001 | 5/1963 | United Kingdom | 424/155 |
| 1241561 | 8/1971 | United Kingdom | 424/155 |
| 1385158 | 2/1975 | United Kingdom | 424/155 |

Primary Examiner—Frederick E. Waddell
Attorney, Agent, or Firm—Oblon, Fisher, Spivak, McClelland & Maier

[57] ABSTRACT

Synthetic magnesium aluminosilicate consisting essentially by weight of 47–57% $SiO_2$, 9–11% $Al_2O_3$, 3–5% MgO, 1–3% CaO, and less than 5% $Na_2O$, balance water to total 100% calculated analytically.

A process for manufacturing, comprising the steps of
stirring into a first aqueous solution, containing the corresponding amounts of magnesium sulfate and aluminum sulfate, a second aqueous solution containing sodium silicate and sodium hydroxide.
thereafter adding a third aqueous solution containing a corresponding amount of calcium chloride,
continuing the stirring,
filtering off and washing the precipitate, and
drying the precipitate at a temperature below 100° C.,
or, instead of adding the third aqueous solution containing calcium chloride, by using lime water in the manufacturing process and for washing.

2 Claims, No Drawings

SYNTHETIC MAGNESIUM ALUMINOSILICATE, PROCESS FOR THE MANUFACTURE THEREOF, AND PHARMACEUTICAL COMPOSITIONS CONTAINING SAME

This invention relates to a synthetic magnesium aluminosilicate, to a process for the manufacture thereof, and to pharmaceutical compositions containing this product.

Synthetically produced magnesium aluminosilicates, which are used particularly for medical purposes, and processes for their manufacture, are known. The criteria applicable for defining an advantageously usable product are essentially: as large a specific surface as possible, good antacid action, and high adsorbency. A process of the type in question for manufacturing a magnesium aluminosilicate is described, for example, in the specification of U.K. Pat. No. 1,385,158.

It is an object of this invention to provide a magnesium aluminosilicate having a well-defined composition which can be manufactured by a simple process hitherto undisclosed and which possesses very good therapeutic properties.

According to the present invention, there is provided a magnesium aluminosilicate characterized in that it substantially comprises, by weight, 47–57% $SiO_2$, 9–11% $Al_2O_3$, 3–5% MgO, 1–3% CaO, and <5% $Na_2O$, calculated analytically.

The composition thereof is comparable to that of natural clays of the palygorskite family. It presents the advantage of being a chemically and physically well-defined synthesis product. It is thus a mineral compound and not a physical mixture of magnesium silicate and aluminum silicate.

Its amorphous state finds its expression in an absence of organized structure on the crystal scale and yields a spectrum of X-ray diffraction which does not exhibit any characteristic line.

There is also provided according to the present invention a process for manufacturing the foregoing magnesium aluminosilicate, characterized by stirring into a first aqueous solution, containing the corresponding amounts of magnesium sulfate and aluminum sulfate, a second aqueous solution, containing sodium silicate and sodium hydroxide, thereafter adding a third aqueous solution containing a corresponding amount of calcium chloride, continuing the stirring, filtering off and washing the precipitate, and drying the precipitate at a temperature below 100° C., or, instead of adding the third aqueous solution containing calcium chloride, by using lime water in the manufacturing process and for washing.

Preferred embodiments of the process according to the invention will now be described in detail, purely by way of example and without implying any limitation of the invention thereto. The concentrations of the liquid starting products are given in percentages by weight.

In a 1000-liter stainless steel vat, 30.76 kg of pharmaceutical-grade (pharmacopie francois 8th edition, 1965 page 665) magnesium sulfate is completely dissolved in 100 liters of lukewarm purified water, the temperature being maintained between 30° and 40° C.

The liquid is then filtered in order to obtain a perfectly clear solution, free of impurities. To this solution there is added 97.5 liters (i.e., 125 kg) of an aqueous solution of pharmaceutical-grade aluminum sulfate ($Al_2O_3$ contents=8%). The whole mixture is homogenized by vigorous stirring, the temperature being kept between 30° and 40° C.

A second solution is also prepared by mixing 182 kg of sodium silicate ($SiO_2$ content=27.5%), previously filtered, 25 liters (i.e., 37 kg) of pharmaceutical-grade caustic soda lye (NaOH content=48%), and 100 liters of purified water.

This second solution is added slowly into the first stirred solution with slow heating to a temperature of 60°–65° C.

Furthermore, 7.8 kg of crystallized pharmaceutical (Pharmacopie francois 8th edition, 1965, page 223) calcium chloride is completely dissolved in 10 liters of lukewarm purified water. The solution is then filtered to obtain a perfectly clear solution which is thereupon added slowly to the mixture, and the latter is then stirred vigorously for about one hour until a homoegneous mixture having a pH of close to 9 is obtained, the pH being taken about every 10 minutes. The resultant precipitate is filtered off in a filter press or a rotary vacuum filter, then washed in copious amounts of water for about 14 hours.

The speed of stirring during precipitation determines the physical texture of the product. Adherence to the specified temperatures makes it possible to obtain the physico-chemical properties.

The precipitate is then dried very gently at the lowest possible temperature, in any case not above 100° C., so as to comprise about 28–32% water by weight.

It has been found that instead of introducing calcium in the form of calcium chloride, it is likewise possible to add calcium together with the water used in the manufacturing process and for washing. For example, by using 10,000 liters of lime water having a calcic ion content of, e.g., 0.01%, it is possible to obtain a CaO content of about 1.4%, analytically calculated, in the end product.

The product obtained by one of the above-mentioned processes is then crushed by means of successive passes through a hammer mill.

The resultant yield is about 95 kg of fine powder, the analytical composition of which is as follow: 51% $SiO_2$, 10% $Al_2O_3$, 4% MgO, 2% CaO, and 1% $Na_2O$, analytically calculated.

Crushing is preferably carried out in such a way that 99% of the powder passes a 100-micron sieve (ASTM 140) and 95% passes a 63-micron sieve (ASTM 215).

An aqueous suspension of 5 g of the powder in 50 ml of distilled water has a pH of 8–10, while calcination at 800° C. leads to a weight loss of about 28–32%.

The resultant product in powder form has a very large specific surface, good antacid action, and high adsorbency, which makes this product particularly suitable for pharmaceutical use in the treatment of gastric and intestinal ailments. The product may either be used alone as a medicinal remedy or be treated to take any desired galenical form known per se for this use. The magnesium aluminosilicate according to the invention may, in the usual manner, be formulated with the aid of additives such as binding agents, viscosity-increasing agents, gelling agents, anti-foaming agents such as dimethyl polysiloxane (Diméticone, DCI), aromatic substances, and similar substances, to take the form of tablets, powder, granules, or a gel.

One particularly advantageous form of preparation for oral administration is an aqueous gel which may be produced by combining conventional gel-forming substances, such as carboxymethyl cellulose, and the aromatic substances, and adding about 30% of the magnesium aluminosilicate according to the invention. An example of the manufacture of such a gel will now be descibed in more detail.

| Manufacture of a preparation in accordance with the invention, in the form of a gel | |
|---|---|
| Starting materials for a 300-kg batch | |
| Magnesium aluminosilicate according to the invention | 90 kg |
| Saccharose | 32 kg |
| Sodium carboxymethyl cellulose | 1.5 kg |
| Preservatives | 0.5 kg |
| Aromatic composition | 33 g |
| Ethanol | 1.2 kg |
| Demineralized water | q.s. for 300 kg |

Manufacture takes place in a vat equipped with a mixer and a homogenizer. The saccharose is dissolved, with stirring, in 160 liters of demineralized water. After filtration, the preservatives are added, and the contents of the vat are brought to a boil for 5 minutes. After cooing, the carboxymethyl cellulose is added, and mixing is carried out until complete dispersion is obtained. The magnesium aluminosilicate according to the invention is then added, the mixture is heated to 90° C. for 1 hour, and stirring is continued for 30 minutes. The result is a gel which is placed in single-dose packets or in bottles, the usual dosage being from 10 to 60 g of gel per day for an adult.

As already mentioned, the magnesium aluminosilicate according to the invention may equally well take other forms of galenical preparations, particularly those of tablets, powder, or granules.

The therapeutic value of the product according to the invention is determined by its physico-chemical characteristics, i.e., by: (a) a very large specific surface resulting in a protectant effect similar to that of bismuth salts used therepeutically, (b) good antacid action, i.e., a rapid neutralizing effect and prolonged buffering action, (c) high adsorbent capacity.

These physico-chemical properties, compared with those of commercially available prior art products, are set forth in the following Table 1.

According to Schnekenburger, an antacid is a good gastric neutralizer when the reaction time for attaining a pH of 3.0 is less than one minute, and when the duration of the action, i.e., the period during which the pH remains above 3.0, is at least 45 minutes. The duration of the action is also called the "buffer effect."

The tests have shown that the initial rise of the pH to 3.0 is very rapid with the compound according to the invention at a concentration of close to 3 g. Among seven other substances (commercially available products) examined, only one raises the pH to 3.0 in less than one minute. The duration of the action of the compound according to the invention is comparable to that of product 2 in Table 1. The buffer effect of the other products used is clearly inferior.

Based upon the aforementioned advantageous properties, the preparation according to the invention is suitable for application in the following fields:

Gastric pathology: gastritis, gastric and duodenal ulcers, reflux esophagitis, hiatus hernia, pregnancy pyrosis, hyperchlorhydria, dyspepsia with meteorism.

Intestinal pathology: diarrhea of any etiology in adults and children, intestinal fermantation, colitic syndrome with fermentation.

Owing to its low toxicity, the product may be used in pediatrics.

TOXICITY STUDIES

Studies of acute, subacute, and chronic toxicity carried out on rats and dogs, 3 months p.o., showed excellent tolerance of the product. No toxic effect could be detected, even at high dosages.

PHARMACOLOGICAL PROPERTIES

In order to check the pharmacological properties in the product, a study of these protective properties was carried out on experimental ulcers induced by means of a hyperglycemic diet.

Forth male Sprague-Dawley rats, weighing from 350 to 380 grams, were divided into four groups of 10 animals each and subjected for 10 days to the high-glucose diet. On the eleventh day, the animals were put to death and their stomachs removed. After the esophageal por-

TABLE 1

| Product | Specific surface $m^2/g$ | Neutralizing capacity ml . 1N HCl/g | Adsorbent capacity at 37° mg methylene blue/g | Dispersing capacity % |
|---|---|---|---|---|
| 1. Magnesium aluminosilicate according to the invention (powder) | 410 | 85 | 109 | 92 |
| 2. Commercially available product (natural magnesium aluminosilicate. powder) | 94 | 42 | 107 | 74 |
| 3. Commercially available product containing bismuth (powder) | 5 | 6 | 25 | 45 |

As may be seen, the physico-chemical properties of the compound according to the present invention are superior to those of the other specialities examined.

Moreover, the neutralizing effect and the buffer capacity in a gastric medium have been the subject of in vitro tests.

tion had been ligatured, the stomachs were emptied and cut open along the lesser curvature, then spread out on a slab of cork. Each stomach was classified from 1 to 3: (0) no ulcer, (1) one to two ulcers, (2) three or four ulcers, and (3) more than four ulcers.

TABLE 2

| Group | Number of rats | Number of stomachs classified | | | | Average classi-fication | % of rats having an ulcer | Index * of ulcer-ation |
|---|---|---|---|---|---|---|---|---|
| | | 0 | 1 | 2 | 3 | | | |
| Control | 10 | 0 | 1 | 0 | 9 | 2.8 | 100 | 280 |
| Compound No. 2 of Table 1 | 9 | 0 | 6 | 1 | 2 | 1.56 | 100 | 156 |
| Compound according to invention (powder) | 9 | 5 | 4 | 0 | 0 | 0.44 | 44 | 196 |
| Composition according to invention (gel) | 10 | 8 | 2 | 0 | 0 | 0.2 | 20 | 4 |

* Total of classifications × % of stomachs having an ulcer / number of animals

Conclusion: In the test on glucose-induced ulcers in rats, the compound according to the invention (gel) proved to be much more effective than the reference product (compound No. 2 of Table 1) and slightly more effective than the active substance in suspension in distilled water.

It has been possible to confirm by means of clinical tests the advantageous properties established in the foregoing tests carried out on animals. The product acts quickly to combat pain and pyrosis, and its activity is remarkable in the case of ulcers, gastritis, and esophagitis. The product is very well tolerated.

CLINICAL STUDIES

In clinical pharmacology, gastric pH measurements were taken with the Heidelberg capsule by means of continuous telemetric recording. Eleven patients suffering from various gastric ailments were analyzed. The average basal pH was 1.16. After administration of 10 g of gel, the maximum pH was, on an average, 4.6. The average time required to reach the maximum pH was 5.7 minutes. The average duration of action, until return to the basal pH, was 29.6 minutes.

Five clinical studies relating to 171 cases demonstrate the therapeutic value of the product according to the invention.

Sixty-nine patients suffering from various gastric complaints (duodenal ulcer, gastric ulcer, gastritis, esophagitis, dyspepsia) were treated for 2 to 3 months with the product according to the invention in gel form, at the rate of 4–6 10-gram packets of gel per day. The product acted rapidly to combat pain and pyrosis. Its activity was remarkable in the case of ulcers, gastritis, and esophagitis. The product was very well tolerated, and its taste was well accepted.

Another group of 40 patients suffering from various gastric complaints was treated for 30 days at the rate of 3–4 10-gram packets per day of gel according to the invention. The results were excellent or good in 75% of the cases. Only 10% (four cases) were judged nil. The improvement was noted above all in connection with such symptoms as pyrosis, distention, and pain. Tolerance was excellent.

Twenty cases of diarrhea of varied etiology were treated at the same dosage for 14 days. The results were good in 80% of the cases and nil in 10%. Tolerance was excellent. Of 16 patients who commented, 13 considered the product better than previous medication, and 3 found it to be equivalent.

In a fourth group (16 cases treated), the results were as follows: 13 excellent, 2 good, 1 nil. The product was considered excellent both as to its action at the gastric level and as to tolerance. The patients found the taste agreeable. In general, the patient considered the product superior to previous medication.

Twenty-six patients were treated for gastric indications. The results were 15 excellent, 9 good, and 2 fair. There were no failures of the medication. Subjective relief of pain was very rapid: on an average in the 26 cases, 8.4 minutes after ingestion.

What is claimed is:

1. A process for manufacturing an amorphous synthetic magnesium aluminosilicate of high adsorbency containing combined CaO and consisting essentially of 47–57% $SiO_2$, 9–11% $Al_2O_3$, 3–5% MgO, 1–3% CaO, and less than 5% $Na_2O$, balance water to total 100%, said percentages being by weight and calculated analytically, comprising the steps of stirring into a first aqueous solution, containing magnesium sulfate and aluminum sulfate, a second aqueous solution containing sodium silicate and sodium hydroxide, thereafter adding a third aqueous solution containing calcium chloride, thereby forming a precipitate, while continuing the stirring, filtering off and washing the precipitate, and drying the precipitate at a temperature below 100° C., the proportions of the reagents and the temperatures in the process being such that precipitate contains combined $SiO_2$, $Al_2O_3$, MgO, CaO and $Na_2O$ within the ratios specified by the above weight percentages and forms at a pH of about 9, and the drying being continued until said water content is obtained.

2. A process for manufacturing an amorphous synthetic magnesium aluminosilicate of high absorbency containing combined CaO and consisting essentially of 47–57% $SiO_2$, 9–11% $Al_2O_3$, 3–5% MgO, 1–3% CaO and less than 5% $Na_2O$, balance water to total 100%, said percentages being by weight and calculated analytically, comprising the steps of:

stirring into a first aqueous solution, containing magnesium sulfate and aluminum sulfate, a second aqueous solution containing sodium silicate and sodium hydroxide, adding lime water, permitting a precipitate to form, while containing the stirring, filtering off and washing the precipitate, and drying the precipitate at a temperature below 100° C., the proportions of the reagents and the temperatures in the process being such that the precipitate contains combined $SiO_2$, $Al_2O_3$, MgO, CaO and $Na_2O$ within the ratios specified by the above weight percentages and forms at a pH of about 9, and the drying being continued until said water cotent is formed.

* * * * *